| United States Patent [19] | [11] Patent Number: 5,021,348 |
|---|---|
| Giesa et al. | [45] Date of Patent: Jun. 4, 1991 |

[54] ATTENUATED HEPATITIS A VIRUS

[75] Inventors: Paula A. Giesa, Lansdale; Maurice R. Hilleman, Lafayette Hill; Philip J. Provost, Harleysville, all of Pa.

[73] Assignee: Merck & Co., Inc., Rahway, N.J.

[21] Appl. No.: 609,677

[22] Filed: May 14, 1984

Related U.S. Application Data

[63] Continuation of Ser. No. 437,095, Oct. 27, 1982, abandoned, which is a continuation-in-part of Ser. No. 71,648, Sep. 4, 1979, abandoned.

[51] Int. Cl.$^5$ ............................................... C12N 7/08
[52] U.S. Cl. ...................................... 435/237; 424/89
[58] Field of Search ......................................... 435/237

[56] References Cited

PUBLICATIONS

Feinstone et al., Science, vol. 182 (Dec. 1973), pp. 1026–1028.
Feinstone et al., J. of Virology, vol. 13, No. 6, Jun. 1974, pp. 1412–1414.
Provost et al., PSEB M, vol. 160 (1979), pp. 213–221.

*Primary Examiner*—Sam Rosen
*Attorney, Agent, or Firm*—Hesna J. Pfeiffer; Donald J. Perrella

[57] ABSTRACT

Hepatitis A virus is attenuated by propagation in cell culture in vitro by direct inoculation of the cell cultures with a human clinical specimen containing the virus.

29 Claims, No Drawings

ATTENUATED HEPATITIS A VIRUS

RELATED APPLICATION

The present application is a continuation of our copending U.S. patent application Ser. No. 437,095 filed Oct. 27, 1982, now abandoned, which in turn is a continuation-in-part of our copending U.S. patent application Ser. No. 71,648 filed Sept. 4, 1979, now abandoned.

BACKGROUND OF THE INVENTION

Prior art methods for obtaining hepatitis A antigen as disclosed by Provost et al., in U.S. Pat. No. 4,029,764 involved intravenous inoculation of a non-human primate with hepatitis A virus with subsequent removal of the infected liver and recovery of virus therefrom. Another method disclosed by Provost et al., in U.S. Pat. No. 4,164,566, involved one or more passages of hepatitis A virus in a sub-human primate, removing infected liver tissue and using such tissue to inoculate an in vitro cell culture, incubating the cell culture until hepatitis A antigen is detectable, and carrying out at least one additional in vitro cell culture passage of the virus. A disadvantage of these processes is that they require the use of primates that are not only expensive but in short supply and difficult to obtain. An in vitro cell culture system which did not require the use of primates would be a significant advance in this art.

OBJECTS OF THE INVENTION

It is an object of the present invention to provide an attenuated hepatitis A virus by in vitro cell culture of hepatitis A virus wherein the inoculum is a human clinical specimen containing hepatitis A virus. Another object is to provide attenuated hepatitis A virus in which the attenuation does not require the use of primates. A further object is to provide a method for the preparation of hepatitis A antigen for use in human vaccines and as a diagnostic antigen. Still another object is to provide an in vitro method for attenuating the virulence of hepatitis A antigen. These and other objects of the present invention will be apparent from the following description.

SUMMARY OF THE INVENTION

Hepatitis A virus is attenuated by propagation in cell culture in vitro by direct inoculation of the cell cultures with a human clinical specimen containing the virus.

DETAILED DESCRIPTION

The present invention relates to the in vitro cell culture attenuation of hepatitis A virus and, more particularly, to in vitro cell culture attenuation of hepatitis A virus wherein the inoculum is a human clinical specimen containing the virus.

The present invention provides a method for propagating hepatitis A virus wherein passage of the virus in a susceptible non-human primate prior to in vitro cell culture is not required.

According to the present invention a clinical specimen containing hepatitis A virus, such as, e.g. stool extract, saliva, urine, or blood, is used as inoculum to infect a susceptible in vitro cell culture. The cell culture may be formed of primary, continuously cultivated, or transformed cells derived from kidney or liver of human or non-human primate origin or diploid fibroblast cells derived from human lung tissue. Specific examples of suitable cell cultures are those derived from fetal or newborn kidney cells from rhesus monkey (FRhK6), cynomolgus monkey, or cercopithecus monkey, or diploid fibroblast cells derived from human or non-human primate lung tissue such as, for example, WI-38 or MRC-5 cell lines. Preferably, the virus first is passed at least once and preferably from about 2 to about 20 times in the foregoing kidney or liver cell cultures and then at least 4 times, preferably from about 5 to about 20 times in diploid fibroblast cells derived from human lung tissue.

The inoculated cell culture is incubated for an extended period of time until positive results are obtained for the presence of hepatitis A antigen. By an extended period of time is meant an incubation of at least about 20 days, and preferably from about 25 up to about 100 days. The incubation is carried out in the presence of a nutrient medium which maintains the cells at temperatures permitting propagation of the virus in the cell culture. Typically, such temperatures are from about 30° to about 39° C., preferably 35° C. The nutrient medium may be, for example, Eagle's Minimum Essential Medium (EMEM), Williams Medium E, Medium 199, Dulbecco's Modified Eagle's Medium, RPMI Media or Basal Medium Eagle with 0.5% fetal calf serum. The cultures are subsequently harvested and serial passages of the viral agent are carried out. As indicated above the virus may be propagated by serial passages in diploid fibroblast cells derived from human lung tissue.

This invention allows diagnosis of hepatitis A disease by direct virus isolation. Further, it allows the in vitro cultivation of the virus in adequate quantity and with appropriate properties for the preparation of a human vaccine and a diagnostic antigen.

Unlike prior art procedures, the present invention permits inoculation of a cell culture from a human clinical specimen instead of infected liver tissue.

The following examples illustrate the present invention without, however, limiting the same thereto.

EXAMPLE 1

A 20 percent extract of human stool in PBS was prepared from acutely ill human hepatitis A patients and clarified by centrifugation. It gave an immune adherence titer of 1:16 for hepatitis A antigen. It was further diluted 1:5 in cell culture medium containing 0.5% fetal calf serum and filtered through a 0.45μ Millipore filter. One ml of this material was inoculated per 25 cm$^2$ flask of fetal rhesus kidney (FRhK6) cells. The inoculum was left in place for 4 hours and then removed. Five ml of EMEM containing 0.5% fetal calf serum plus neomycin and glutamine were added per flask and the medium removed and renewed at 5-7 day intervals with incubation at 32°-35° C. Coverslips were removed periodically and examined by the direct immunofluorescence technique (Provost et al., P.S.E.B.M., 160, 213-221, 1979) for hepatitis A antigen. Such examination was essentially negative until day 33 post inoculation, when the first clear positive results were obtained. The cultures were subsequently harvested at day 37 and the cells disrupted by freeze-thawing and sonication. Cellular debris was removed by low speed centrifugation. The supernatant product gave a positive result by radioimmunoassay for hepatitis A antigen.

EXAMPLE 2

A second passage of the virus in FRhK6 cells was achieved by inoculating 0.5 ml of the supernatant product from Example 1 into fresh cell cultures, which were handled comparably to those above. Fluorescence antibody examination revealed the first clear evidence of virus presence at day 15 post-inoculation. The cultures were harvested at day 19 post-inoculation and the product gave a positive result for hepatitis A antigen by radioimmunoassay. Additional serial passage of the virus was carried out in cell culture, i.e., passages 3, 4 and 5. By passage 5, heavy virus growth occured as early as 7-14 days and the virus harvest at day 14 gave strong positive results for hepatitis A antigen by both immune adherence (IA) and radioimmune assay (RIA).

EXAMPLE 3

Antigen, 0.05 ml, obtained as described in Example 2, was incubated with human convalescent hepatitis A sera, 0.02 ml of a 1:20 dilution. The mixture was incubated at 37° C. for 1 hour and then held at 4° for a period of three hours. A drop of the material was placed onto a carbon-coated, 300-mesh copper grid, and allowed to adsorb for 30 seconds. The grid was then stained for 2 minutes with 2% aqueous phosphotungsic acid, pH 6.0 (adjusted with 1N KOH) and examined in a Philips 300 electron microscope at 80 KV. After reaction with hepatitis A antibody, characteristics halos of antibody molecules were seen to surround the numerous 27 m$\mu$ hepatitis A virus particles and to bind them into an immune complex.

EXAMPLE 4

The final infected cell culture harvests obtained from Example 2, prepared under aseptic conditions, were treated with 1:4000 formalin at 37° C. for 72 hours. Excess residual formalin was neutralized with sodium bisulfite. All treatments were peformed under aseptic conditions. The product was stored at 4° C. Subcutaneous or intramuscular injection of 4 doses of 1 ml given at 2 week intervals into S. mystax marmosets and guinea pigs induced circulating hepatitis A antibody in these animals. Further, the marmosets were rendered resistant to challenge with virulent doses of hepatitis A virus.

EXAMPLE 5

Hepatitis A virus derived as in Example 1 was serially passaged a total of 15 times in fetal rhesus monkey kidney cells at 35° C. The virus harvest from passage 15 was then successfully propagated in human diploid lung (HDL) cell cultures at 35° C. A total of 10 serial in vitro passages of the virus in HDL were carried out. After such passages the hepatitis A virus was attenuated in virulence for both marmosets (S. labiatus) and chimpanzees in that intravenous inoculation into these animals produced no serum enzyme elevations (e.g., isocitric dehydrogenase) and only minor changes in liver histopathology while at the same time eliciting a hepatitis A antibody response. All animals inoculated with the attenuated virus resisted challenge with 1000 50% infectious doses of virulent hepatitis A virus injected intravenously. Thus the tissue culture-passaged hepatitis A virus constituted a live, attenuated hepatitis A vaccine.

What is claimed is:

1. A method of attenuating the virulence of hepatitis A virus comprising passaging the virus at least once in a tissue culture in which hepatitis A virus is capable of replicating using as inoculum a human clinical specimen containing hepatitis A virus.

2. A method according to claim 1 wherein the tissue culture is a primary or continuously cultivated or transformed cell culture derived from kidney or liver of human or non-human primate origin, or diploid fibroblast cells derived from human lung tissue.

3. A method according to claim 2 comprising at least one first passage in a primary or continuously cultivated or transformed cell culture derived from kidney or liver of human or non-human primate wherein the inoculum is a human clinical specimen containing hepatitis A virus, and at least four passages in diploid fibroblast cells derived from human lung tissue.

4. A method according to claim 3 wherein the virus is passaged from about 2 to about 20 times in the kidney or liver cell culture.

5. A method according to claim 3 wherein the virus is passaged from about 5 to about 20 times in diploid fibroblast cells derived from human lung tissue.

6. A method according to claim 3 wherein the primary or continuously cultivated or transformed cell culture is kidney of fetal or newborn rhesus, cynomolgus or cercopithecus monkeys.

7. A process for propagating human hepatitis A virus in vitro in cell culture comprising inoculating a cell culture in which hepatitis A virus is capable of replicating using as inoculum a human clinical specimen containing hepatitis A virus but in which clinical specimen hepatitis A virus is not capable of replicating, incubating the susceptible cell culture until the presence of hepatitis A virus is detected in the susceptible cell culture, and harvesting the hepatitis A virus from the cell culture.

8. A process according to claim 7 wherein the human clinical specimen is selected from stool extract, saliva, urine or blood.

9. A process according to claim 7 wherein the susceptible cell culture comprises a primary or continuously cultivated or transformed cell culture derived from kidney or liver of human or non-human primate origin or diploid fibroblast cells derived from human lung tissue.

10. In the method for direct isolation of HAV taken from stool samples of humans with acute hepatitis A, and further isolating and propagating the virus in a suitable substrate, the step which comprises directly passaging said virus in African Green Monkey kidney culture cells to form a serological test or radioimmunoassay of anti-HAV.

11. In the method of claim 10 for the in vitro propagation of hepatitis A virus by cultivating HAV in primary African Green Monkey kidney (AGMK) cell cultures, the step which comprises directly and serially passaging the virus at least five times in AGMK without inter position of a mammalian model.

12. The method of claim 10 in which the isolated virus is serially passaged at least five times in AGMK.

13. A process which comprises culturing unmodified HAV on human kidney cells (HKC) and harvesting the thus-produced viruses.

14. A process which comprises culturing on HKC isolated viruses produced by the process of claim 13 and isolating thus-produced viruses.

15. A process for increasing the growth rate of HAV cultured on HKC which comprises (a) the process of claim 14, (b) culturing the resulting isolated viruses on HKC and isolating thus-produced viruses and (c) repeating step (b) a number of times, each with isolated viruses from the immediately preceding culturing on HKC.

16. A process of claim 15 which comprises from about five to ten successive culturing steps.

17. A process of claim 13 wherein the HAV is Hepatitis-A virus isolate of human origin.

18. A process of claim 17 wherein the HAV consists essentially of that isolated from stool.

19. A process of claim 13 which consists essentially of culturing HAV on HKC.

20. A process according to claim 14 or claim 15 which comprises isolating from the final culturing step those viruses which grow most rapidly and/or are produced in largest quantities.

21. A process according to claim 14 or claim 15 which comprises (a) selecting from each culturing step those viruses which grow most rapidly and/or are produced in largest quantities and (b) culturing only thus-selected viruses in any immediately succeeding culturing step.

22. Modified HAV adapted to HKC (HAV/HKC) and having a rate of growth and/or a rate of proliferation significantly greater than that of unmodified HAV cultured on HKC.

23. A process which comprises culturing the modified virus of claim 22 on human fibroblast strains (HFS).

24. A process which comprises culturing on HFS isolated viruses produced by the process of claim 23 and isolating thus-produced viruses.

25. A process for increasing the growth rate of HAV/HKC cultured on HFS which comprises (a) the process of claim 24 (b) culturing the resulting isolated viruses on HFS and isolating thus-produced viruses and (c) repeating step (b) a number of times, each with isolated viruses from the immediately preceding culturing on HFS.

26. A process of claim 25 which comprises from about 50 to 75 successive culturing steps.

27. A process according to claim 25 or claim 26 which comprises (a) selecting from each culturing step those viruses which grow most rapidly and/or proliferate in greatest quantities and (b) culturing only thus-selected viruses in any immediately succeeding culturing step.

28. Modified HAV according to claim 22 and further adapted to HFS (HAV/HFS) and having a rate of growth and/or a rate of proliferation significantly greater than that of modified HAV according to claim 22 and cultured on HFS.

29. A process which comprises:
(a) culturing unmodified HAV on human kidney cells (HKC) and harvesting thus-produced viruses,
(b) culturing isolated viruses from step (a) and HKC and isolating thus-produced viruses,
(c) culturing isolated viruses from step (b) on HKC and isolating thus-produced viruses,
(d) repeating step (c) a number of times, each with isolated viruses from the immediately preceding culturing on HKC to obtain HAV adapted to HKC (HAV/HKC) and having a rate of growth and/or a rate of proliferation significantly greater than that of HAV cultured on HKC, the isolated viruses cultured in and isolated from the products of steps (b) through (d) being those which grow rapidly and/or are produced in largest quantities;
(e) culturing HAV/HKC isolated from step (d) on human fibroblast strains (HFS) and isolating thus-produced viruses,
(f) culturing isolated viruses from step (e) on HFS and isolating thus-produced viruses,
(g) culturing isolated viruses from step (f) on HFS and isolating thus-produced viruses,
(h) repeating step (g) a number of times, each with isolated viruses from the immediately preceding culturing on HFS to obtain HAV adapted to HFS (HAV/HFS) and having a rate of growth and/or a rate of proliferation significantly greater than that of HAV/HKC cultured on HFS,
the isolated viruses cultured in and isolated from the products of steps (e) through (h) being those which grow most rapidly and/or are produced in largest quantities.

* * * * *

REEXAMINATION CERTIFICATE (2237th)

United States Patent [19]

Giesa et al.

[11] B1 5,021,348

[45] Certificate Issued  Mar. 1, 1994

[54] ATTENUATED HEPATITIS A VIRUS

[75] Inventors: Paula A. Giesa, Lansdale; Maurice R. Hilleman, Lafayette Hill; Philip J. Provost, Harleysville, all of Pa.

[73] Assignee: Merck & Co., Inc., Rahway, N.J.

Reexamination Request:
No. 90/002,770, Jul. 1, 1992

Reexamination Certificate for:
Patent No.: 5,021,348
Issued: Jun. 4, 1991
Appl. No.: 609,677
Filed: May 14, 1984

Related U.S. Application Data

[63] Continuation of Ser. No. 437,095, Oct. 27, 1982, abandoned, which is a continuation-in-part of Ser. No. 71,648, Sep. 4, 1979, abandoned.

[51] Int. Cl.$^5$ ............................................. C12N 7/08
[52] U.S. Cl. ..................................... 435/237; 424/89
[58] Field of Search ............... 424/89; 435/235.1, 236, 435/237, 239

[56] References Cited

U.S. PATENT DOCUMENTS

| | | |
|---|---|---|
| 3,105,011 | 9/1963 | McLean et al. |
| 3,354,038 | 11/1967 | Bass et al. |
| 3,432,391 | 3/1969 | Hays et al. |
| 3,470,294 | 9/1969 | Drager et al. |
| 3,520,972 | 7/1970 | Smith et al. |
| 3,871,954 | 3/1975 | Zuckerman . |
| 3,935,066 | 1/1976 | Apostolov . |
| 4,029,764 | 6/1977 | Provost et al. |
| 4,031,203 | 6/1977 | Provost et al. |
| 4,053,582 | 10/1977 | Stickl . |
| 4,058,598 | 11/1977 | Stern et al. |
| 4,164,566 | 8/1979 | Provost et al. |
| 4,506,016 | 3/1985 | Flehmig . |
| 4,532,215 | 7/1985 | Daemer et al. |
| 4,614,793 | 9/1986 | Hughes et al. |
| 4,783,407 | 11/1988 | Provost et al. |
| 4,844,228 | 1/1990 | Purcell et al. |
| 5,021,348 | 6/1991 | Giesa et al. |

FOREIGN PATENT DOCUMENTS

| | | |
|---|---|---|
| 2398504 | 2/1979 | European Pat. Off. |
| 0025745 | 3/1981 | European Pat. Off. |
| 0074119 | 8/1982 | European Pat. Off. |
| 811411 | 4/1959 | United Kingdom . |
| 878704 | 10/1961 | United Kingdom . |

OTHER PUBLICATIONS

Rightsel et al. Science, 124, pp. 226–228 (1956).
O'Malley et al. Proc. Soc. Exp. Biol. Med., 108, pp. 200–205 (1961).
Liebhaber et al. J. Exp. Med., 122, p. 1135, (1965).
O'Malley, et al., Proc. Nat. Acad. Sci., 56, p. 895 (1965).
Mirkovic et al., Proc. Soc. Exp. Biol. Med., 138, p. 626, (1971).
Advances in Viral Hepatitis, W.H.O. Tech. report, Series No. 602, (1977).
Dienstag et al., Intervirl., 6, p. 319, (1976).
Provost et al., Pro. Soc. Exp. Bio. & Med., 160, p. 213 (1979).
Provost et al., Biol. Abstract, 68, ref. No. 12885.
Feinstone et al., J. of Vir., 13, No. 6, pp. 1412–1414 (1974).
Feinstone et al., Science, 182, pp. 1026–1028 (1973).
Frosner et al., Infection, 7, 303–305 (1979).
Zuckerman, Nature, 279, p. 579 (1979).
Purcell et al., Am. J. Med. Sci. 270, 61–71 (1975).
McCollum, J. of Med. Virology 8: 1–29 (1981).
Flehming et al. Med. Micro. Immunol. 170: 83–89 (1981).
Ed. Gerety, R. J. Hepatitis A pp. 247–261 Acad. Press (1984).
Ed. Gerety, R. J. Hepatitis A pp. 33–46 Acad. Press (1984).
Bradley, et al. Char. of Hepatitis A Virus, pp. 876–889, (1976).
Deinhardt, et al. Int. Symp. O. Viral Hep. Milon, Dev. Biol. Stand., 30, 390–404 (1975).
Almond Attn. of Poliovirus Neurovirulence, 41: 153–180 (1987).
Westrop et al. J. of Virl. 63: 1338–1344 (1989).
Gauss-Muller et al. J. of Med. Vir. 7: 233–239 (1981).

Cann et al. Nucleic Acids Research 12: 7787-7792 (1984).
Pilipenko et al. Virology 168: 201-209 (1989).
Monica et al. J. of Virology pp. 515-525 (1986).
Kawamura et al. J. of Virology pp. 1302-1309 (1989).
Siegl et al. J. of Virology pp. 40-47 (1978).
Frosner et al. J. of Med. Vir. 1: 163-173 (1977).
Lennette, et al. eds; Diag. Proc. For Viral Rickettsial and Chlamydial Inf. 5th ed, p. 907 (1979).
Kojima et al, J. Med. Virol, 7, 273-286 (1981).
Provost et al, J. Med. Virol, 20, 165-175 (1986).
Roberston et al, J.I.D., 163, 286-292 (1991).
Provost, et al., P.S.E.B.M. 142, 1257 (1974).
Mascoli et al., P.S.E.B.M. 142, 276 (1973).
Dienstag, et al. Lancet, 705, Apr. 5, 1975.
Flehmig et al., Viral Hepatitis and Liver Disease, 87-90 (1988).
Flemig et al, Viral Hepatitis and Liver Disease, 100-105 (1988).
Flehmig et al., 3, Med. Viral 22, 7-16 (1987).
Provost, P. J. and Hilleman, M. R. Hepatitis Scientific Memoranda, Memo H-1531, early Feb. 1979.
Divizia, et al., Microbiologica 9, pp. 269-278, (1986).
Cromeans, et al, Viral Hepatitis and Liver Disease, 24-26 (1988).
Divizia, et al., Viral Hep. and Liver Disease, 27-30, (1988).
Provost, P. J. in Hep. A Gerety ed. Ch. 13, pp. 245-261, (1984).
Provost and Hilleman, P.S.E.B.M. 159, 201-203 (1978).
ATCC, 1992 Catalog on Cell Lines & Hybridomas, pp. 43, 44, 98 & 101.
Zachoval, et al., in Hepatitis A, Chap. 3, Gerety ed., pp. 33-46 (1984).
Latner, Clinical Biochemistry, pp. 553-559 (1975).
Goodheart, An Intro. to Virology, pp. 63, 177-178, 180-182, 199-200 (1969).
Dick, Immunisation, pp. 8-10, 68, 120, 133-134 (1978).

*Primary Examiner*—Sam Rosen

[57] ABSTRACT

Hepatitis A virus is attenuated by propagation in cell culture in vitro by direct inoculation of the cell cultures with a human clinical specimen containing the virus.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-29 is confirmed.

* * * * *